United States Patent [19]

Seri et al.

[11] Patent Number: 5,138,039
[45] Date of Patent: Aug. 11, 1992

[54] CHELATING COMPOUNDS AND THEIR USE

[75] Inventors: Shigemi Seri, Kimitsu; Hirohiko Yamauchi; Makoto Azuma, both of Ichihara; Yoji Arata, Tokyo, all of Japan

[73] Assignee: Nihon Medi-Physics Co., Ltd, Hyogo, Japan

[21] Appl. No.: 745,393

[22] Filed: Aug. 15, 1991

Related U.S. Application Data

[62] Division of Ser. No. 682,080, Apr. 9, 1991.

[30] Foreign Application Priority Data

Apr. 10, 1990 [JP] Japan .................................. 2-094353

[51] Int. Cl.$^5$ ...................... C07F 13/00; A61K 49/02
[52] U.S. Cl. ......................... 534/14; 534/10; 424/1.1
[58] Field of Search ........................ 424/1.1; 534/10, 14

[56] References Cited

U.S. PATENT DOCUMENTS

| | | | |
|---|---|---|---|
| 4,352,751 | 10/1982 | Wieder et al. | 424/1.1 X |
| 4,418,208 | 11/1982 | Nunn et al. | 424/1.1 X |
| 4,647,447 | 3/1987 | Gries et al. | 424/9 |
| 4,943,523 | 7/1990 | Stavrianopoulos | 534/14 X |
| 4,957,939 | 9/1990 | Gries et al. | 514/492 |
| 4,963,344 | 10/1990 | Gries et al. | 424/9 |

FOREIGN PATENT DOCUMENTS 58-28718  2/1983  Japan .

OTHER PUBLICATIONS

Deutsch, E., et al, Nucl. Med. Biol., vol. 13, No. 4, pp. 465–475 (1986).
Narabayashi, I, et al, Annals of Nuclear Medicine, vol. 1, No. 1, 39–42 (1987).
Pavone, P., Radiology, vol. 176, No. 1, pp. 61–64 (Jul. 1990).
Saha, G. B., et al, The Journal of Nuclear Medicine and Allied Sciences, vol. 33, No. 1, pp. 1–6 (Jan.–Mar. 1989).
Brown, et al. *J. Nucl. Med.*, vol. 22(2), "Radiation Dose Calculation for Tc-99m", pp. 177–183, 1981.
Costello, et al, J. Nucl. Med. 24(4), "The Investigation of Radiopharmaceutical Components . . . ", pp. 353–355, 1983.

*Primary Examiner*—John S. Maples

[57] ABSTRACT

A chelating compound of the formula:

$$(R-NHOC-CH_2)_n-A-(CH_2COOH)_m \qquad (I)$$

wherein R is an aromatic ring-containing organic group, A is a residue of an aminopolyacetic acid excluding acetic acid groups ($-CH_2COOH$) therefrom, m is an integer of at least two and n is an integer of 1 or 2, or its salt, which has a specificity to a hepatobiliary system so that a complex formed between said chelating compound and a metallic element through a coordinate bond is useful and a diagnostic or therapeutic agent for hepatobiliary organs and tissues.

9 Claims, 1 Drawing Sheet

Fig. 1: Scintigram of hepatoma-transplanted
rat using In-111-B-DNS-etn-DTPA
(70 hours after administration)
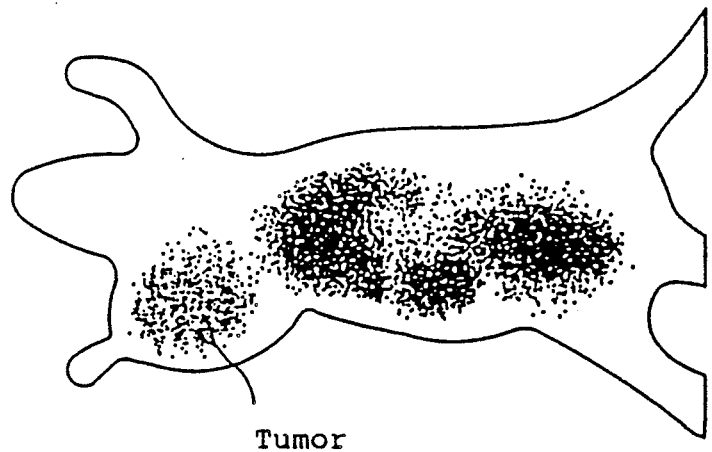
Tumor

CHELATING COMPOUNDS AND THEIR USE

This is a divisional of copending application Ser. No. 07/682,080, filed Apr. 9, 1991.

The present invention relates to chelating compounds and their use. More particularly, it relates to chelating compounds having a chelating property and a specificity or selectivity for a hepatobiliary system, and their use as carriers for metal elements suitable for diagnosis or therapy of hepatobiliary organs or tissues.

In recent years, patients suffered from diseases in a hepatobiliary system such as hepatoma are significantly increased, and it is highly demanded to establish a reliable diagnostic method, particularly through imaging, as well as an effective therapeutic method.

Among various imaging agents for hepatobiliary organs or tissues as heretofore reported, there is known technetium-99m-N-pyridoxyl-5-methyltryptophan (Tc-99m-PMT). Imaging with this complex is well evaluated in showing a significant specificity to hepatocellular carcinoma (Hasegawa et al.: Cancer, 57, 230–236 (1986)). Unfortunately, its sensitivity is however somewhat low as 60%. Diethylenetriaminepentaacetato gadolinium (Gd-DTPA) is also known as a nuclear magnetic resonance (NMR) imaging agent (Weinmann et al.: AJR, 142, 619–629 (1984)). However, it is excreted into urine so quickly that its distribution in liver is insufficient and satisfactory informations on liver are hardly obtainable.

As well known, aminopolycarboxylic acids have an excellent chelating property and are useful as carriers for metallic elements suitable for diagnosis. Thus, the complex formed between aminopoly-carboxylic acids and metallic elements are used as imaging agents for radioactive diagnosis, nuclear magnetic resonance (NMR) diagnosis, etc.

It has now been found that the introduction of a certain aromatic ring-containing organic group into an aminopolycarboxylic acid is effective in enhancing the specificity or selectivity for a hepatobiliary system. For instance, when DTPA (diethylenetriaminepentaacetic acid) is administered intravenously into an animal, it is mainly excreted into urine. In contrast, it was experimentally confirmed that N,N''-bis[(2-dansylaminoethyl)carbamoylmethyl]-diethylene-triamine-N,N',N''-triacetic acid (B-DNS-etn-DTPA) obtained by introducing two dansyl groups into DTPA is excreted mainly into intestine through a hepatobiliary system.

As stated above, aminopolycarboxylic acids are well known chelating compounds. Since the coordinate bond formed between aminopolycarboxylic acids and metallic elements are generally stable in an animal or at a physiological pH range, they are practically used as carriers for metallic elements to make imaging agents, for instance, Gd-DTPA as above mentioned. However, it has never been known that their specificity or selectivity for a hepatobiliary system is significantly enhanced by introducing a certain aromatic ring-containing organic group therein.

SUMMARY OF THE INVENTION

The present is based on the above finding and provides a chelating compound which has a high specificity or selectivity for a hepatobiliary system and is useful as a carrier for a metallic element to give a diagnostic or therapeutic agent for hepatobiliary organs and tissues.

The chelating compound of the invention is an aminopolycarboxylic acid, particularly an aminopolyacetic acid, in which one or two carboxylic groups are each combined with an aromatic ring-containing organic group, particularly through an amide (—CONH—) bond and at least two carboxylic groups are each kept in a free or salt form to have a chelating property with a metallic element.

More specifically, the chelating compound is representable by the formula:

$$(R-NHOC-CH_2)_n-A-(CH_2-COOH)_m \qquad (I)$$

wherein R is an aromatic ring-containing organic group, A is a residue of an aminopolyacetic acid excluding acetic acid groups (—CH$_2$COOH) therefrom, m is an integer of at least two and n is an integer of at least one. The carboxyl groups therein may be in a free or salt form.

BRIEF DESCRIPTION OF THE DRAWINGS

FIG. 1 depicts the scintigram obtained in Example 12.

DETAILED DESCRIPTION OF THE INVENTION

The aminopolyacetic acid comprises a hydrocarbon chain in a straight, branched or cyclic form, at least two amino groups introduced in the hydrocarbon chain (such as —C—NH—C—) and/or at the end of the hydrocarbon chain (such as —C—NH$_2$), and each of at least three acetic acid groups (—CH$_2$—COOH) attached to a nitrogen atom in said amino groups. For example, such aminopolyacetic acid includes ethylenediamine-tetracetic acid (EDTA), diethylenetriamine pentaacetic acid (DTPA), trans-1,2-cyclohexadiamine tetraacetic acid (CyDTA), 1,4,7,10-tetraazacyclododecane tetraacetic acid (DOTA), etc. As to other specific examples of the aminopolyacetic acid, reference may be made to JP-A-58/29718 (DE-A-3129906).

In the chelating compound of the invention, at least two acetic acid groups originated from the aminopolyacetic acid are kept in a free or salt form such as an alkali metal salt so as to capture a metallic element through a covalent bond, while at least one acetic acid group is combined with the aromatic ring-containing organic group. Preferably, the aromatic ring-containing organic group is originated from an aromatic ring-containing organic amine, and the combination between the aminopolyacetic acid and the aromatic ring-containing organic amine is made through a carbonamide (—CONH—) linkage.

As the aromatic ring-containing organic group, there are exemplified aryl, alyl(lower)alkyl, arylsulfonyl, aryl(lower)alkylsulfonyl, arylamino(lower)alkyl, aryl(lower)alkylamino(lower)alkyl, arylsulfonylamino(lower)alkyl, aryl(lower)alkylsulfonylamino(lower)alkyl, etc. The aryl portion, of which examples are phenyl, naphthyl, etc., in these groups may be optionally substituted with lower alkyl (e.g. methyl, ethyl), lower alkylamino (e.g. methylamino, ethylamino), di(lower)alkylamino (e.g. dimethylamino, diethylamino), etc. Thus, specific examples of the aromatic ring-containing organic group represented by the symbol R are phenyl, lower alkylphenyl such as tolyl (e.g. p-tolyl), di(lower)alkylaminophenyl such as dimethylaminophenyl (e.g. p-dimethylaminophenyl), phenyl(lower)alkyl such as phenethyl, benzenesulfonylamino(lower)alkyl such as benzenesulfonylaminoethyl, lower alkylbenzenesulfonylamino(lower)alkyl such as toluenesulfonylaminoethyl (e.g. ptoluenesulfonylaminoethyl), di(lower)alkylaminonaphthalenesulfonylamino(lower)alkyl such as dimethylaminonaphthalenesulfonylaminoethyl or dimethylaminonaphthalenesulfonylaminohexyl, naphthylamino(lower)alkyl such as naphthylaminoethyl, naphthyl(lower)alkyl such as naphthylmethyl, naphthalenesulfonylamino(lower)alkyl such as naphthalenesulfonylaminoethyl, etc., among which naphthyl(lower)alkyl, naphthylamino(lower)alkyl, naphthalenesulfonylamino(lower)alkyl, 5-dimethylaminonaphthalene-1-sulfonylamino(lower)alkyl (i.e. dansylamino(lower)alkyl), etc. are favorable.

Production of the chelating compound of the invention may be achieved by a per se conventional procedure for formation of an amide bond between an amino group and a carboxyl group, for instance, reacting an aromatic ring-containing organic amine of the formula: R—NH$_2$ (wherein R is as defined above) with an aminopolyacetic acid of the formula: (HOOCCH$_2$-)$_n$—A—(CH$_2$COOH)$_m$ (wherein A, m and n are each as defined above) in any reactive form. The reaction may be carried out usually in an inert solvent (e.g. tetrahydrofuran, dioxane, dimethylformamide, benzene, toluene), if necessary, in the presence of the agents such as a base, a dehydrating agent, etc. to condense. Depending on the reaction conditions, particularly the proportion of the aromatic ring-containing organic amine to the aminopolyacetic acid, there is produced the desired chelating compound having one or two aromatic ring-containing organic groups as the major product. When their mixture is obtained, the mono-substituted product and the bissubstituted product can be easily separated by a per se conventional separation procedure such as chromatography. In general, the bis-substituted product is favorable, because of its higher specificity or selectivity for a hepatobiliary system.

The thus obtained chelating compound can be converted into the corresponding complex by treatment with a metal element in a per se conventional procedure for complexation. The kind of the metal element may be appropriately chosen depending on the purpose for which the complex is used.

For the nuclear medicine such as scintigraphical diagnosis or radio therapy, various radioactive metal elements may be used. For instance, the use of such gammaray emitting metal elements as technetium-99m, indium-111 and gallium-67 are preferred in order to produce tumorimaging agents. On the other hand, beta-ray emitting metal elements such as rhenium-186, rhenium-188 and yttrium-90 are clinically useful for treatment of tumors.

For instance, B-DNS-etn-DTPA as an example of the invention is promptly excreted from the normal or healthy liver to bile ducts, but when a tumor is present in liver, it is difficulty excreted to bile ducts, because no efficient bile duct exists in the tumor lesion. Utilizing this dynamic behavior, a complex of B-DNS-etn-DTPA with indium-111 is used as a radioactive imaging agent for diagnosis of a hepatobiliary system, and a complex of B-DNS-etn-DTPA with rhenium-186 may be employed to irradiate the tumor lesion in liver for the therapeutic purpose.

Metallic elements usable for NMR imaging are required to be paramagnetic, and their preferred examples are lanthanoid elements under Atomic Nos. 57 to 70 and transition metal atoms under Atomic Nos. 21 to 29, 42 and 44. Among them, gadolinium, dysprosium, etc. are especially preferred because of their strong magnetic moment and chemical stability. These paramagnetic metallic elements are often toxic in concentrations required for NMR imaging, and therefore their amounts to be introduced into animals are desired to be kept as little as possible. The administration of those paramagnetic metallic elements in the form of complexes with the chelating compounds of the invention is quite advantageous, because the toxicity of the metallic elements are suppressed by the complexation and also their amounts to be administered for effective NMR imaging are lowered due to their specificity assuring an efficient accumulation at the target organ or tissue in a hepatobiliary system.

For instance, diethylenetriamine-pentaacetato gadolinium(III) (Gd-DTPA) is normally administered on the clinical use by intravenous injection at a dose of 100 μmol/kg. Since its distribution is not however specific for a hepatobiliary system, the excretion into urine is made promptly. As the result, sufficient contrast useful for diagnosis can be obtained only over a period of time producing the differences in concentration among tissues or organs. In fact, the administration of Gd-DTPA to rats at a dose of 50 μmol/mg does not produce any change of signal intensity in liver (Kawamura et al.: Image Information, 21, 206–207 (1989)). Administration of a complex of Gd(III) with N-[(2-dansylaminoethyl)carbamoylmethyl]-diethylenetriamine-N,N',N'',N'''-tetraacetic acid (Gd(III)-DNS-etn-DTPA) to rats produces enhancement of the $T_1$ relaxation in liver even at such a small dose as 20 μmol/kg, and this effect remains for one hour after the administration. Thus, Gd(III)-DNS-etn-DTPA is specifically taken up into liver so that satisfactory NMR imaging can be obtained even at a low dose.

When the use for X-ray diagnosis is aimed at, the chelating compound of the invention may be complexed with a metallic element from Atomic Nos. 57 to 83, particularly lanthanum to form a complex.

Practical and presently preferred embodiments of the invention are illustratively shown on the following Examples.

EXAMPLE 1

Preparation of N-[(2-dansylaminoethyl)carbamoylmethyl]-diethylenetriamine-N,N',N'',N'''-tetraacetic acid (DNS-etn-DTPA)(2) and N,N''-bis[(2-dansylaminoethyl)carbamoylmethyl]-diethylenetriamine-N,N',N'''-triacetic acid (B-DNS-etn-DTPA)(3):

A. N-Dansyl-ethylenediamine (1)

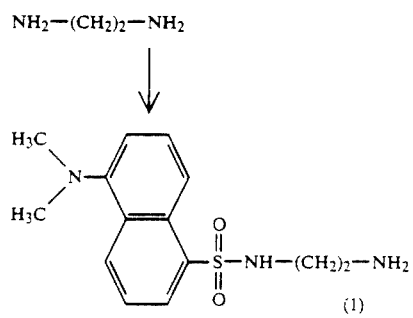

To a solution of ethylenediamine (635 mg, 10.6 mmol) in chloroform (10 ml), a solution of dansyl chloride (285 mg, 1.06 mmol) in chloroform (12 ml) was dropwise added, and the reaction mixture was stirred at room temperature overnight, followed by addition of a bit of 1 N sodium hydroxide thereto for hydrolysis of unreacted dansyl chloride. The reaction mixture was concentrated, and the residue was combined with acetone. Insoluble materials were removed by filtration, and the filtrate was concentrated. Water (50 ml) was added to the residue, and extracted with ethyl acetate three times. The organic layer was dried over anhydrous sodium sulfate and concentrated. The residue was dissolved in a small amount of ethyl acetate, a bit of n-hexane was added thereto, and the resultant mixture was allowed to stand at room temperature overnight. The precipitate was collected and recrystallized from ethyl acetate to give Compound (1) (124 mg). Yield, 63 %.

B. DNS-etn-DTPA (2) and B-DNS-etn-DTPA (3)

FAB-MS (negative): m/z 667 (M-H)$^-$, 689 (M+Na−2H)$^-$, m/z 711 (M+2Na−3H)$^-$.

Elemental analysis for $C_{28}H_{38}N_6O_{11}S_1Na_2 \cdot 4\frac{1}{2}H_2O$(%): Calcd.: C, 42.37; H, 5.97; N, 10.59; S, 4.04. Found: C, 41.94; H, 5.70; N, 10.99; S, 4.06.

Compound (3): IR (KBr) cm$^{-1}$: $SO_2$—NH (1140, 1320), $COO^-$ (1410, 1590), CO—NH (1660, 3400), $C_{10}H_6$—N—$(CH_3)_2$ (2800), $CH_2$ (2950).

FD-MS: m/z 945 (M+H).

Elemental analysis for $C_{42}H_{54}N_9O_{12}S_2Na_3 \cdot 8H_2O$ (%): Cacld.: C, 43.71; H, 6.11; N, 10.92; S, 5.56. Found: C, 43.54; H, 5.52; N, 10.51; S, 5.89.

EXAMPLE 2

Preparation of N-[(6-dansylaminohexyl)carbamoylmethyl]-diethylenetriamine-N,N',N'',N''-tetraacetic acid (DNS-hxn-DTPA)(5) and N,N''-bis[(6-dansylaminohexyl)carbamoylmethyl]-diehtylenetriamine-N,N,,N''-triacetic acid (B-DNS-hxn-DTPA)(6):

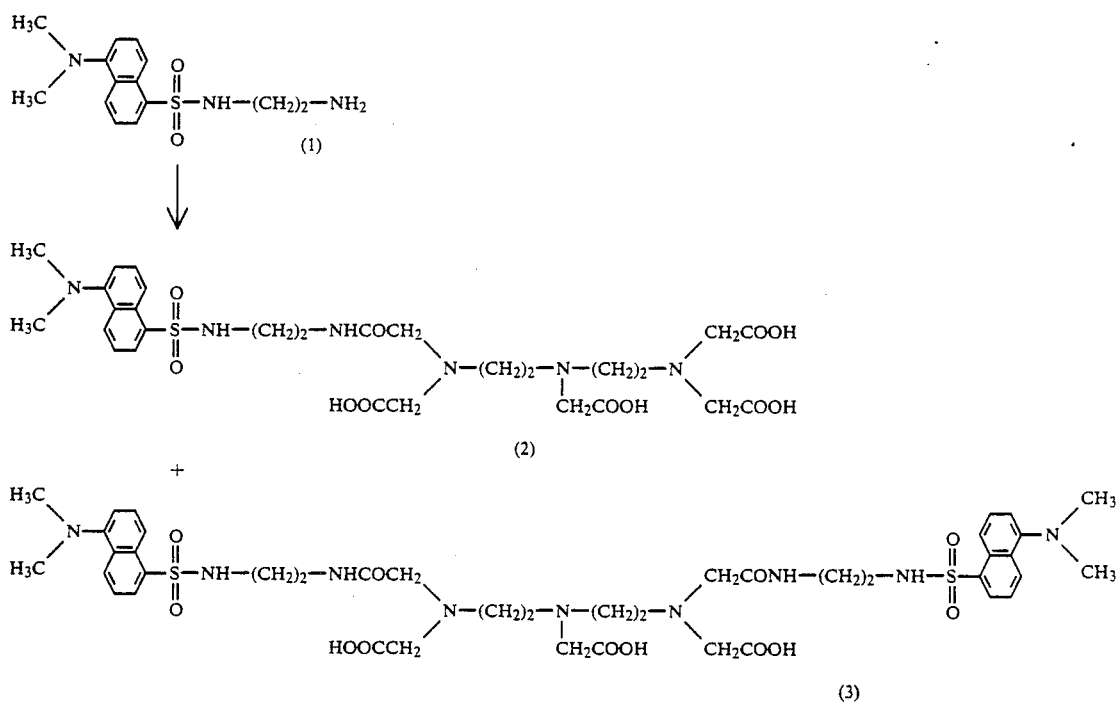

Diethylenetriamine-N,N,',N',N'',N''-pentaacetic acetic anhydride (DTPA) (1.39 g, 3.89 mmol) was dissolved in dimethylformamide (30 ml) with heating, and the resultant solution was cooled to room temperature. A solution of Compound (1) (113 mg, 0.385 mmol) in dimethylformamide (5 ml) was dropwise added thereto with stirring, and the reaction was carried out at room temperature for 1.5 hours. After concentration, the residue was combined with 0.1 M carbonate buffer (pH 9.0, 20 ml) and carried out on anionic resin exchange chromatography (resin: AG-X4; eluent: 0.3-3M formic acid) and thin layer chromatography (supporting layer: silica.gel 60; developing solvent: ethanol/ aqueous ammonia=4/1) for purification, whereby Compound (2) (69 mg) and Compound (3) (72 mg) respectively in yields of 27% and 20%.

Compound (2): IR (KBr) cm$^{-1}$: $SO_2$—NH (1140, 1320), $COO^-$ (1400, 1590), CO—NH (1660, 3420), $C_{10}H_6$—N—$(CH_3)_2$ (2800), $CH_2$ (2950).

A. N-Dansyl-hexamethylenediamine (4)

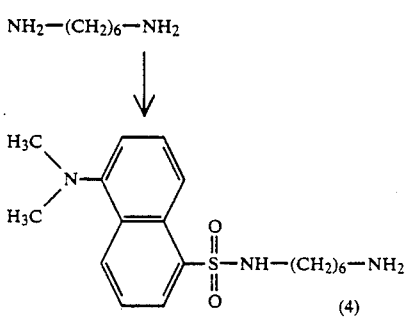

Hexamethylenediamine (5.39 g, 45.9 mmol) was combined with dimethylformamide (15 ml), and a solution of dansyl chloride (2.40 g, 8.7 mmol) in dimethylformamide (10 ml) was dropwise added thereto, followed by stirring at room temperature for 4 hours. Insoluble materials were removed by filtration, and the filtrate was stirred at room temperature overnight. After concentration, water and ethyl acetate were added to thereto, and 1 N hydrochloric acid was added thereto to adjust the aqueous layer to pH 4. The aqueous layer was washed with ethyl acetate three times, adjusted to pH 11 with potassium carbonate and extracted with ethyl acetate twice. The extracts were collected, washed with water three times, dried over anhydrous sodium sulfate and concentrated to give Compound (4) (1.04 g) as an oil.

Compound (5): IR (KBr) cm$^{-1}$: SO$_2$—NH (1140, 1320), COO$^-$ (1410, 1590), CO—NH (1660, 3420), C$_{10}$H$_6$—N—(CH$_3$)$_2$ (2800), CH$_2$ (2950).

FAB-MS (negative): m/z 745 (M+Na—2H)$^-$, m/z 761 (M+K—2H)$^-$, m/z 767 (M+2Na—3H)$^-$, m/z 783 (M+Na+K—3H)$^-$.

Elemental analysis for C$_{32}$H$_{46}$N$_6$O$_{11}$S$_1$Na$_2$·6H$_2$O (%): Calcd.: C 43.83; H, 6.67; N, 9.58; S, 3.66. Found: C, 43.24; H, 6.43; N, 10.35; S, 3.73.

C. B-DNS-hxn-DTPA (6)

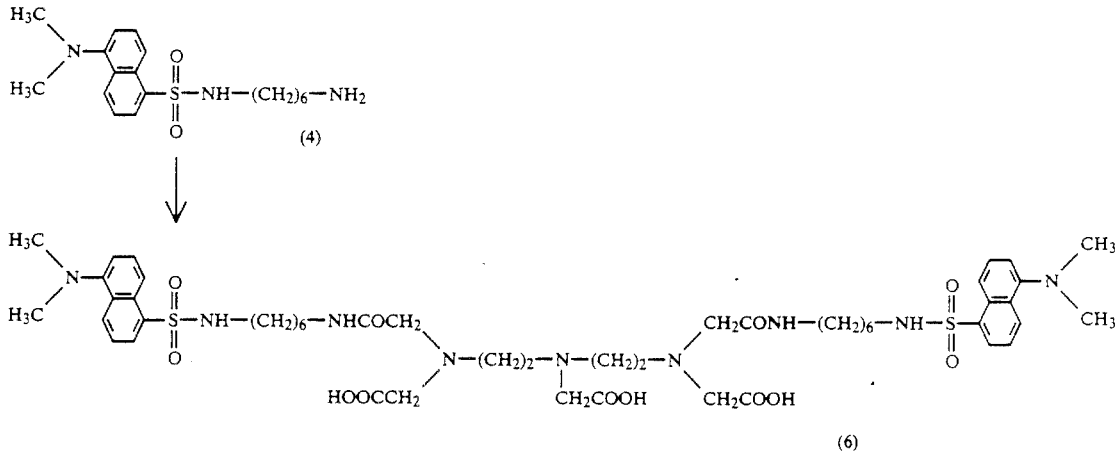

Yield, 34%.

B. DNS-hxn-DTPA (5)

The insoluble materials as removed in the above B were collected and dissolved in methanol. The resultant

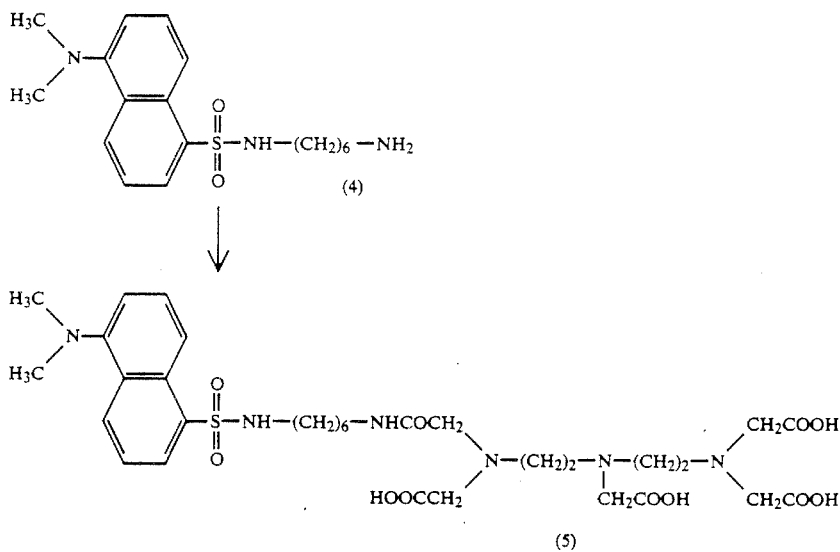

DTPA anhydride (777 mg, 2.18 mmol) was dissolved in dimethylformamide (20 ml) under heating, and the resultant solution was cooled to room temperature. A solution of Compound (4) (130 mg, 0.372 mmol) in dimethylformamide (5 ml) was dropwise added thereto with stirring, and the reaction was carried out at room temperature for 1 hour. After concentration, the residue was combined with 1 M carbonate buffer (pH 9.0, 50 ml) and allowed to stand in a refrigerator overnight. Insoluble materials were removed by filtration, and the filtrate was treated in the same manner as in Example 1 B. to give Compound (5) (47 mg). Yield, 17 %.

solution was concentrated, and the residue was carried out on thin layer chromatography for purification, whereby Compound (6) (24 mg) was obtained. Yield, 6%.

Compound (6): IR (KBr) cm$^-$: SO$_2$—NH (1140, 1310), COO$^-$ (1400, 1580), CH$_2$ (1450, 2930),

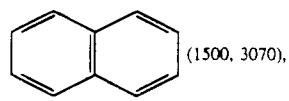 (1500, 3070),

CO—NH (1660 3400), C$_{10}$H$_6$—N—(CH$_3$)$_2$ (2780).

FAB-MS (negative): m/z 1054 (M-H)$^-$, m/z 1076 (M+Na−2H)$^-$, m/z 1092 (M+K−2H)$^-$.

Elemental analysis for $C_{50}H_{71}N_9O_{12}S_2Na_2 \cdot 7H_2O$ (%): Calcd.: C, 48.97; H, 6.99; N, 10.28; S, 5.23. Found: C, 48.56; H, 6.44; N, 10.01; S, 5.05.

EXAMPLE 3

Preparation of N-[[2-(1-naphthylamino)ethyl]carbamoylmethyl]-diethylenetriamine-N,N',N'',N''-tetraacetic acid (8):

A. N-1-Naphthylethylenediamine (7)

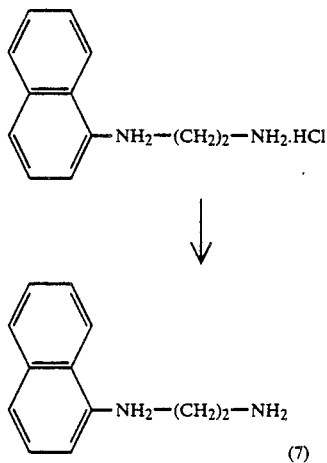

To a suspension of N-1-naphthylethylenediamine dihydrochloride (746 mg, 2.88 mmol) in chloroform (50 ml), a saturated solution of sodium hydrogen carbonate (50 ml) was added, and the resultant mixture was stirred. The organic layer was collected, washed with a saturated solution of sodium chloride twice, dried over anhydrous sodium sulfate and concentrated to give Compound (7) (310 mg) as an oil. Yield, 58%.

B. N-[[2-(1-Naphthylamino)ethyl]carbamoylmethyl]-diethylenetriamine-N,N',N'',N''-tetraacetic acid (8)

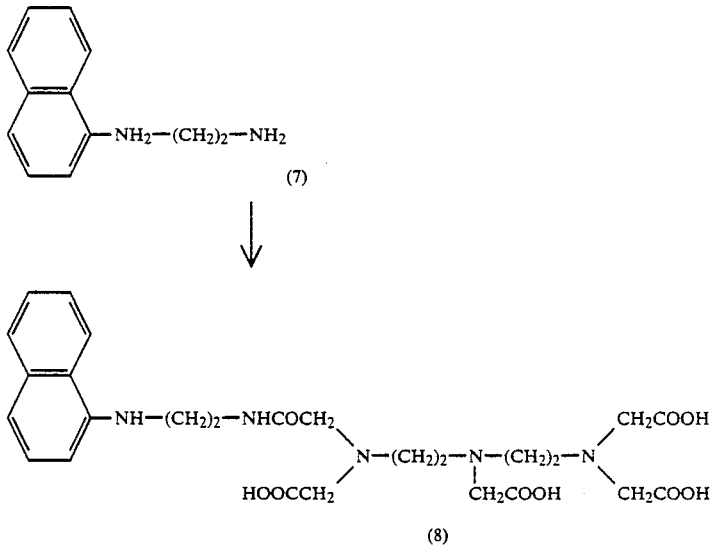

DTPA anhydride (2.02 g, 5.60 mmol) was dissolved in dimethylformamide (20 ml) with heating and cooled to room temperature. A solution of Compound (7) (218 mg, 1.17 mmol) in acetone (5 ml) was added thereto with stirring, and the reaction was carried out at room temperature for 1.5 hours. The resultant mixture was allowed to stand at room temperature in a dark box overnight. The reaction mixture was treated with activated charcoal and concentrated. To the residue, 0.1 M carbonate buffer (pH 8.9, 20 ml) was added, and the resultant mixture was treated with activated charcoal, followed by concentration. The residue was dissolved in 0.1 M carbonate buffer (pH 8.9, 15 ml), treated with activated charcoal and carried out on anionic exchange resin chromatography (resin: AG-X4, eluent: 1.2–4.8 M formic acid) and thin layer chromatography to give Compound (8) (34 mg). Yield, 5%.

Compound (8): IR (KBr) cm$^{-1}$: COOC$^-$ (1400, 1580), CO—NH (1660, 3400), CH$_2$ (2960).

FAB-MS (positive): m/z 606 (M+2Na−H)$^+$, m/z 622 (M+K+Na−H)$^+$, m/z 650 (M+4Na−3H)$^+$.

Elemental analysis for $C_{26}H_{33}N_5O_9Na_2 \cdot 6H_2O$ (%): Calcd.: C, 43.76; H, 6.36; N, 9.81. Found: C, 43.81; H, 6.09; N, 10.58.

EXAMPLE 4

Preparation of N,N''-bis(1-naphthylmethyl-carbamoylmethyl)-diethylenetriamine-N,N',N'',N''-triacetic acid (9):

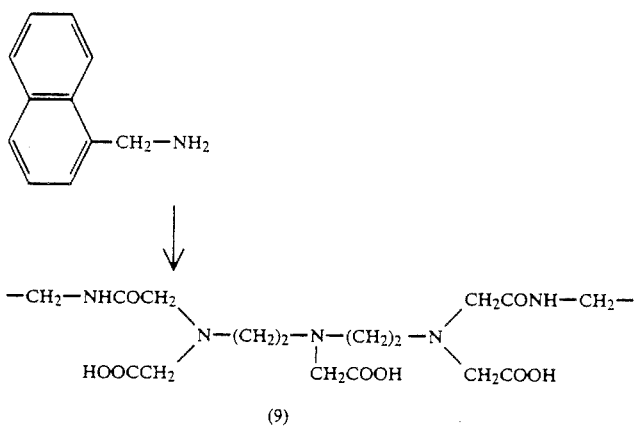

(9)

DTPA anhydride (2.05 g, 5.74 mmol) was dissolved in hot dimethylformamide (20 ml) with heating and cooled to room temperature. A solution of 1-naphthalenemethylamine (467 mg, 2.88 mmol) in acetone (5 ml) was dropwise added thereto, and the resultant mixture was stirred at room temperature for 2 hours. After concentration, 0.1 M carbonate buffer (pH 8.9, 30 ml) was added to the residue. Insoluble materials were collected, dissolved in methanol with heating and then cooled. After removal of insoluble materials by filtration, the filtrate was concentrated. The residue was dissolved in a small amount of dimethylformamide and carried out on thin layer chromatograph for purification, whereby Compound (9) (114 mg) was obtained. Yield, 6 %.

Compound (9): IR (KBr) cm$^{-1}$: COO$^-$ (1400, 1590),

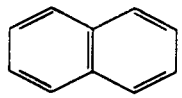

(1510, 3050), CO—NH (1650, 3400), CH$_2$ (2950).

FAB-MS (positive): m/z 710 (M+K)$^+$, m/z 732 (M+K+Na−H)$^+$, m/z 748 (M+2K−H)$^+$.

Elemental analysis for C$_{36}$H$_{40}$N$_5$O$_8$Na$_1$·5H$_2$O (%): Calcd.: C, 55.17; H, 6.43; N, 8.94. Found: C, 54.82; H, 6.08; N, 9.65.

EXAMPLE 5

Preparation of N-[[2-(1-naphthalenesulfonylamino)-carbamoylmethyl]-diethylenetriamine-N,N', N'',N'''-tetraacetic acid (11):

A. N-(1-Naphthalenesulfonyl)-ethylenediamine (10)

NH$_2$—(CH$_2$)$_2$—NH$_2$

↓

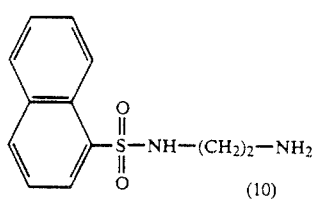

(10)

To a solution of ethylenediamine (1.06 g, 17.6 mmol) in dimethylformamide (10 ml), triethylamine (1.79 g, 17.7 mmol) was added, followed by stirring. With stirring at room temperature, a solution of 1-naphtalenesulfonyl chloride (4.00 g, 17.6 mmol) in dimethylformamide (15 ml) was dropwise added thereto, and the reaction was carried out in an ice bath for 1 hour. Insoluble materials were removed by filtration, and the filtrate was concentrated. To the residue, chloroform and water were added, and insoluble materials were filtered off. Furthermore, the aqueous layer was separated, washed with ethyl acetate twice and adjusted to pH 11 with potassium carbonate, followed by extraction with ethyl acetate three times. The extracts were collected, washed with water twice, dried over anhydrous sodium sulfate and concentrated. The residue was allowed to stand in a refrigerator overnight, and the precipitate was collected and recrystallized from ethyl acetate to give Compound (10) (153 mg). Yield, 4%.

B. N-[[2-(1-Naphthalenesulfonylamino)ethyl]carbamoylmethyl]-diethylenetriamine-N,N', N'',N'''-tetraacetic acid (11)

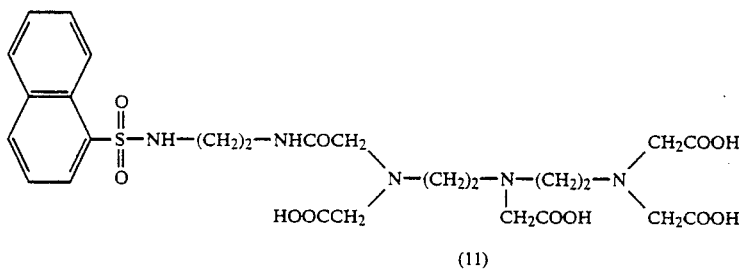

(11)

DTPA anhydride (996 mg, 2.79 mmol) was dissolved in dimethylformamide (20 ml) with heating, and the resultant solution was cooled to room temperature. A solution of Compound (10) (139 mg, 0.557 mmol) in acetone (20 ml) was dropwise added thereto at room temperature with vigorous stirring. After the addition, the resultant mixture was stirred at room temperature for 1 hour and then allowed to react overnight. After concentration, the residue was dissolved in 0.1 M carbonate buffer (pH 8.9, 15 ml) and then treated in the same manner as in Example 1 B to give Compound (11) (66 mg). Yield, 19%.

Compound (11): IR (KBr) cm$^{-1}$: $SO_2$—NH (1160, 1320), $COO^-$ (1400, 1590), $CH_2$ (2870), CO—NH (3420).

FAB-MS (negative): m/z 646 $(M+Na-2H)^-$, m/z 662 $(M+K+2H)^-$, m/z 668 $(M+2Na-3H)^-$, m/z 684 $(M+Na+K-3H)^-$.

Elemental analysis for $C_{26}H_{34}N_5O_{11}S_1 \cdot 6H_2O$ (%): Calcd.: C, 41.32; H, 6.14; N, 9.27; S, 4.24. Found: C, 41.05; H, 5.55; N, 9.96; S, 4.23.

From the results of the elemental analysis as above, the products in Examples 1 to 11, i.e. Compounds (2), (3), (5), (6), (8), (9) and (11), were obtained in the form of sodium salt. This is probably due to sodium salt in the supporting layer used in thin layer chromatography at the stage of purification.

EXAMPLE 6

In-111-DNS-etn-DTPA (complex):

A. Preparation of In-111 complex with Compound (2)

Compound (2) (0.93 mg, 1.39 μmol) was dissolved in 0.2 M acetate buffer (pH 5.3, 0.46 ml), and the similar buffer (pH 5.3, 0.46 ml) containing indium chloride ($^{111}$In, 69.1 MBq) was added thereto. The resultant mixture was shaken for 30 seconds to give In-111-DNS-etn-DTPA.

B. Behavior of In-111-DNS-etn-DTPA on thin layer chromatography

An appropriate amount of In-111-DNS-etn-DTPA was spotted onto a silica gel plate (silica gel 60 manufactured by Merck Co., Ltd.) at a distance of 2 cm from the bottom and developed for 10 cm using a mixture of methanol-acetic acid (5 : 3) as a developing solvent. After air-drying, the plate was scanned with a thin layer radiochromatoscanner (Aloca Co.) to determine the distribution of radioactivity, and the radiochemical purity was calculated with a data processing apparatus (D-2000, manufactured by Hitachi Ltd.).

As the result, a single radioactivity peak (Rf=0.13) was observed. Since the Rf value of this peak is different from that (Rf=0) of indium acetate ($^{111}$In) or indium chloride ($^{111}$In) as a possible radiochemical impurity, the radiochemical purity of In-111-DNS-etn-DTPA was determined to be 100%.

C. Behavior of In-111-DNS-etn-DTPA on electrophoresis

An appropriate amount of In-111-DNS-etn-DTPA was spotted on an acetylated cellulose membrane and subjected to electrophoresis using 50 mM phosphate buffer (pH 7.4) with a constant current of 1 mA/cm at room temperature for 30 minutes. In the same manner as in the above B, the membrane was scanned with a thin layer radiochromatoscanner to determine the distribution of radioactivity. As the result, it was revealed that In-111-DNS-etn-DTPA is a complex having a single negative charge.

EXAMPLE 7

Other In-111 complexes:

In the same manner as in Example 6 A, B and C, In-111 complexes with Compounds (3), (5), (6), (8), (9) and (11) were prepared, and their behaviors on thin layer chromatography (TLC) and electrophoresis (EP) as well as their radiochemical purity were determined. The results are shown in Table 1.

TABLE 1

| Carrier compound | TLC (Rf) | EP | Radiochemical purity (%) |
|---|---|---|---|
| (3) | 0.12 | — | 100 |
| (5) | 0.14 | Negative | 100 |
| (6) | 0.08 | — | 100 |
| (8) | 0.19 | Negative | 100 |
| (9) | 0.20 | Positive | 100 |
| (11) | 0.24 | Negative | 100 |

EXAMPLE 8

Gd-DNS-etn-DTPA (complex):

Compound (2) (21.0 mg, 31.4 μmol) was dissolved in 0.2 M acetate buffer (pH 5.3, 5 ml), and 1.97 ml of a $10^{-3}$ N hydrochloric acid (10.5 ml) containing $GdCl_3 \cdot 6H_2O$ (93.3 mg, 0.251 mmol) were added thereto. The resultant mixture was shaken for 1 minute and concentrated. The residue was dissolved in water (2 ml) and subjected to high performance liquid chromatography for purification, followed by lyophilization to give Gd-DNS-etn-DTPA (20.3 mg). Yield, 79%.

IR (KBr) cm$^{-1}$: $SO_2$—NH (1150, 1320), $COO^-$ (1410, 1590), $C_{10}H_6$—N—$(CH_3)_2$ (2800), $CH_2$ (2950), CO—NH (3400).

FAB-MS (positive): m/z 823 $M^+$, m/z 845 $(M+Na-H)^+$.

Elemental analysis for $C_{28}H_{37}N_6O_{11}S_1Gd_1 \cdot 9H_2O$ (%): Calcd.: C, 34.1; H, 5.6; N, 8.5; S, 3.3. Gd, 16.0. Found: C, 33.4; H, 4.7; N, 8.4; S, 3.5; Gd, 15.4.

EXAMPLE 9

Eu-DNS-etn-DTPA (complex) and La-DNS-etn-DTPA (complex):

In the same manner as in Example 8 but using $EuCl_3 \cdot 6H_2O$ or $LaCl_3 \cdot 7H_2O$, the Eu or La complex with Compound (2) was prepared. There was thus obtained Eu-DNS-etn-DTPA (19.4 mg) in a yield of 77% or La-DNS-etn-DTPA (14.4 mg) in a yield of 61%.

Eu-DNS-etn-DTPA: IR (KBr) $cm^{-1}$: $SO_2$-NH (1150, 1330), COO= (1410, 1600), $C_{10}H_6$—N—$(CH_3)_2$ (2800), $CH_2$ (2960), CO—NH (3420).

FAB-MS (negative): m/z 817 (M-H)$^-$.

Elemental analysis for $C_{28}H_{37}N_6O_{11}S_1Eu_1 \cdot 7\frac{1}{2}H_2O$ (%): Calcd.: C, 35.3; H, 5.5; N, 8.8; S, 3.4; Eu, 15.9. Found: C, 35.1; H, 4.6; N, 8.7; S, 4.0; Eu, 15.0.

La-DNS-etn-DTPA: IR (KBr) $cm^{-1}$: $SO_2$—NH (1150, 1330), COO$^-$ (1410, 1590), $C_{10}H_6$—N—$(CH_3)_2$ (2800), $CH_2$ (2950), CO—NH (3420).

FAB-MS (negative): m/z 803 (M-H)$^-$.

Elemental analysis for $C_{28}H_{37}N_6O_{11}S_1La_1 \cdot 8H_2O$ (%): Calcd.: C, 35.4; H, 5.6; N, 8.9; S, 3.4; La, 14.6. Found: C, 34.7; H, 4.4; N, 8.7; S, 2.9; La, 13.7.

EXAMPLE 10

Radioactivity distribution of In-111-DNS-etn-DTPA and In-111-B-DNS-etn-DTPA in rats on intravenous injection:

In-111-DNS-etn-DTPA or In-111-B-DNS-etn-DTPA was intravenously injected to Sprague-Dawley rats (female) at a dose of 25 μg/rat, and the rats were sacrificed one hour thereafter to take out various organs. The radioactivity in each organ was measured, and the results are shown in Table 2.

TABLE 2

| | Radioactivity distribution of In-111-DNS-etn-DTPA and In-111-B-DNS-etn-DTPA in rats (% injected dose/organ) | |
|---|---|---|
| Organ | In-111-DNS-etn-DTPA | In-111-B-DNS-etn-DTPA |
| Liver | 1.35 | 2.60 |
| Bowel | 68.01 | 91.86 |
| Kidney | 1.00 | 0.26 |
| Urinary bladder | 25.49 | 3.86 |
| Blood (1 ml) | 0.06 | 0.03 |
| Others | 7.97 | 2.74 |

From the above results, it is suggested that In-111-B-DNS-etn-DTPA is an excellent radioactive diagnostic agent for examination of hepatobiliary tissues.

For comparison, the radioactivity distribution of In-111-DTPA (In-111 complex with DTPA), prepared as in Example 6 A, in rats on intravenous injection was determined as above. As the result, it was revealed that about 90% of the injected radioactivity was excreted in urine within one hour after the administration.

It is thus found that the excretion route of DTPA is changed to a hepatobiliary system by introduction of a dansyl group therein. In other words, a dansyl group may be concluded to be effective in the construction of a hapatobiliary tissue-specific carrier.

EXAMPLE 11

Radioactivity distribution of In-111-DNS-hxn-DTPA and In-111-B-DNS-hxn-DTPA in rats on intravenous injection:

In-111-DNS-hxn-DTPA or In-111-B-DNS-hxn-DTPA was intravenously injected to Sprague-Dawley rats (female) at a dose of 25 μg/rat, and the rats were sacrificed one hour thereafter to take out various organs. The radioactivity in each organ was measured, and the results are shown in Table 3.

TABLE 3

| | Radioactivity distribution of In-111-DNS-hxn-DTPA and In-111-B-DNS-hxn-DTPA in rats (% injected dose/organ) | |
|---|---|---|
| Organ | In-111-DNS-hxn-DTPA | In-111-B-DNS-hxn-DTPA |
| Liver | 0.51 | 1.82 |
| Bowel | 93.42 | 92.81 |
| Kidney | 0.05 | 0.12 |
| Urinary bladder | 5.35 | 0.46 |
| Blood (1 ml) | 0.01 | 0.05 |
| Others | 0.65 | 4.45 |

From the above results, it is found that like In-111-B-DNS-etn-DTPA, tested In-111 complexes are both excellent diagnostic agents for hepatobiliary tissues.

EXAMPLE 12

Imaging of rat hepatoma in rat with In-111-B-DNS-etn-DTPA:

In-111-B-DNS-etn-DTPA was injected into a hepatoma-transplanted WKA-rat (male, tumor size: about 3 cm) intravenously injected at a dose of 50 μg/rat and kept in a cage for 70 hours. The rat was fixed and subjected to image with a gamma-camera (manufactured by Toshiba, Ltd.). The posterior scintigram thus obtained is shown in FIG. 1 of the accompanying drawings. While the radioactivity was taken up in liver and bowel, the tumor (at the left shoulder of the rat) was clearly visualized.

From the above results, it is clear that In-111-B-DNS-etn-DTPA is taken up into hepatoma.

EXAMPLE 13

A. Relaxation of Gd-DNS-etn-DTPA

Gd-DNS-etn-DTPA as obtained in Example 8 was dissolved in 10 mM acetate buffer (pH 5.5), and the relaxation time ($T_1$ and $T_2$, millisecond) was measured with regard to water proton by NMR (manufactured by Nihon Denshi; 270 MHz; 25° C.). The results are shown in Table 4.

TABLE 4

| Concentration (mM) | $T_1$ | $T_2$ |
|---|---|---|
| 5.59 | 44 | 36 |
| 1.31 | 313 | 246 |
| 0.66 | 534 | 424 |
| 0 | 3260 | 1315 |

From the above results, Gd-DNS-etn-DTPA shows an excellent relaxation time. For instance, the $T_1$ and $T_2$ values of water were shortened about 74 times and about 37 times at a concentration of 5.59 mM, respectively.

B. Pharmacodynamics on relaxation of Gd-DNS-etn-DTPA in mice:

To each of ICR mice (female), a solution of Gd-DNS-etn-DTPA in 10 mM acetate buffer (pH 5.5) was intravenously administered at a dose of 0.02 mM/kg by injection. The mice were sacrificed by cutting their necks at 1 minute, 1 hour and 6 hours after the administration. The proton relaxation value of each selected organ was measured in a test tube by NMR (270 MHz)

at 25° C. Relaxation of $T_1$ and $T_2$ on each organ is shown in Table 5.

TABLE 5

| Organ | Normal value | | After 1 min. | | After 60 min. | | After 360 min. | |
| --- | --- | --- | --- | --- | --- | --- | --- | --- |
| | $T_1$ | $T_2$ | $T_1$ | $T_2$ | $T_1$ | $T_2$ | $T_1$ | $T_2$ |
| Liver | 1040 | 17 | 776 | 16 | 745 | 17 | 1025 | 19 |
| Heart | 1484 | 29 | 1289 | 28 | 1408 | 26 | 1523 | 29 |
| Kidney | 1269 | 31 | 918 | 28 | 878 | 29 | 1196 | 33 |
| Brain | 1576 | 45 | 1556 | — | 1586 | 51 | 1613 | 50 |
| Blood | 1755 | 53 | 884 | — | 1713 | 67 | 1680 | 54 |

From the above results, it is revealed that Gd-DNS-etn-DTPA is quickly taken up by liver, kidney and heart in mouse and excreted. Since the change of $T_1$ in liver and kidney with time is distinguished from that of $T_1$ in blood, the behavior of Gd-DNS-etn-DTPA in liver and kidney may be considered to be not originated from that in blood. Furthermore, Gd-DNS-etn-DTPA may be found to afford an influence on the $T_1$ relaxation in a living body.

What is claimed is:

1. A complex which comprises a chelating compound and a radioactive metallic element coordinately bound thereto, said chelating compound having the formula:

$$(R-NHOC-CH_2)_n-A-(CH_2-COOH)_m \quad (I)$$

wherein R is naphthyl, naphthyl(lower)alkyl, naphthylsulfonyl, naphthyl(lower)alkylsulfonyl, naphthylamino)lower)alkyl, naphthyl(lower)alkylamino(-lower)alkyl, naphthylsulfonylamino(lower)alkyl or naphthyl(lower alkylsulfonylamino)lower)alkyl, the naphthyl moiety being optionally substituted with lower alkyl, lower alkylamino or di(lower)alkylamino, A is a residue of an aminopolyacetic acid excluding acetic acid groups ($-CH_2COOH$) therefrom, m is an integer of at least 2 and n is an integer of 1 or 2, or its salt.

2. The complex according to claim 1, wherein R is dansyl.

3. The complex according to claim 1, wherein R is dansylamino(lower)alkyl.

4. The complex according to claim 1, wherein the aminopolyacetic acid comprises a hydrocarbon chain in a straight, branched or cyclic form, at least two amino groups in the hydrocarbon chain, at the terminal position or in the hydrocarbon chain and at the terminal position, and at least three acetic acid ($-CH_2COOH$) groups attached to the same or different nitrogen atoms in said amino groups.

5. The complex according to claim 1, wherein the aminopolyacetic acid is ethylenediamine tetraacetic acid (EDTA), diethylenetriamine pentaacetic acid (DTPA), trans-1,2-cyclohexadiamine tetraacetic acid (CyDTA) or 1,4,7,10-tetraazacyclododecane tetraacetic acid (DOTA).

6. The complex according to claim 1, wherein the radioactive metallic element is technetium-99m, indium-111, rhenium-186, rhenium-188 or yttrium-90.

7. A diagnostic agent for hepatobiliary organs or tissues which comprises a complex according to claim 1.

8. A therapeutic agent for hepatobiliary organs or tissues which comprises a complex according to claim 1.

9. A complex which comprises a chelating compound and a radioactive metallic element coordinately bound thereto, said chelating compound having the formula $$(R-NHOC-CH_2)_n-A-(CH_2COOH)_m \quad (I)$$

wherein R is an aromatic ring-containing organic group, A is a residue of an aminopolyacetic acid excluding acetic acid groups ($-CH_2COOH$) therefrom, said aminopolyacetic acid being a member selected from the group consisting of ethylenediamine tetraacetic acid (EDTA), diethylenetriamine pentaacetic acid (DTPA), trans-1,2-cyclohexadiamine tetraacetic acid (CyDTA) and 1,4,7,10-tetraazacyclododecane tetraacetic acid (DOTA), m is an integer of at least 2 and n is an integer of 1 or 2, or its salt.

* * * * *

UNITED STATES PATENT AND TRADEMARK OFFICE
CERTIFICATE OF CORRECTION

PATENT NO. : 5,138,039
DATED : August 11, 1992
INVENTOR(S) : Shigemi Seri et al

It is certified that error appears in the above-identified patent and that said Letters Patent is hereby corrected as shown below:

Claim 1 (column 17, line 35), change "thylamino)lower)alkyl" to --thylamino(lower)alkyl--.

Claim 1 (column 17, line 37), change "naphthyl(lower alkylsulfonylamino) lower)alkyl" to --naphthyl(lower)alkylsulfonylamino(lower)alkyl--.

Signed and Sealed this

Third Day of August, 1993

Attest:

MICHAEL K. KIRK

Attesting Officer

Acting Commissioner of Patents and Trademarks